United States Patent
Klee

(10) Patent No.: US 6,494,078 B1
(45) Date of Patent: Dec. 17, 2002

(54) RETENTION-TIME LOCKED COMPREHENSIVE MULTIDIMENSIONAL GAS CHROMATOGRAPHY

(75) Inventor: Matthew S. Klee, Wilmington, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/888,927

(22) Filed: Jun. 25, 2001

(51) Int. Cl.⁷ .................. G01N 30/02; G01N 21/01; B01D 15/08
(52) U.S. Cl. ............ 73/23.35; 73/23.36; 73/23.22; 73/23.27; 210/198.2; 210/656; 422/89; 55/37
(58) Field of Search .............. 73/23.35, 23.22, 73/23.36, 23.27, 23.39, 23.24, 23.23; 55/67; 210/198.2, 656; 422/70, 89

(56) References Cited

U.S. PATENT DOCUMENTS

| | | | | |
|---|---|---|---|---|
| 3,043,127 A | * | 7/1962 | DeFord et al. .................. 73/23 |
| 3,057,183 A | * | 10/1962 | De Ford ........................ 73/23 |
| 3,824,838 A | * | 7/1974 | Ohtsu et al. .................... 73/23.1 |
| 4,824,446 A | * | 4/1989 | Mowery et al. ................. 55/67 |
| 4,994,096 A | * | 2/1991 | Klein et al. ..................... 55/20 |
| 5,009,099 A | * | 4/1991 | Wells et al. .................... 73/1 G |
| 5,106,756 A | * | 4/1992 | Zaromb ........................ 436/161 |
| 5,116,764 A | * | 5/1992 | Annino et al. ................ 436/161 |
| 5,163,979 A | * | 11/1992 | Patrick et al. .................. 55/21 |
| 5,281,397 A | * | 1/1994 | Ligon .......................... 422/89 |
| 5,339,673 A | * | 8/1994 | Nakagawa et al. ......... 73/23.36 |
| 5,398,539 A | * | 3/1995 | Gordon et al. .............. 73/23.35 |
| 5,405,432 A | * | 4/1995 | Snyder et al. ................. 95/82 |
| 5,436,166 A | * | 7/1995 | Ito et al. ...................... 436/161 |
| 5,492,555 A | * | 2/1996 | Strunt et al. ................... 95/86 |
| 5,524,084 A | * | 6/1996 | Wang et al. ................. 364/510 |
| 5,542,286 A | * | 8/1996 | Wang et al. ................ 73/23.22 |
| 5,559,728 A | * | 9/1996 | Kolwalski et al. ..... 364/571.02 |
| 5,670,379 A | * | 9/1997 | Ito et al. ...................... 436/161 |
| 5,827,946 A | * | 10/1998 | Klee et al. .................. 73/23.36 |
| 5,987,959 A | * | 11/1999 | Klee et al. .................... 73/1.02 |
| 6,153,438 A | * | 11/2000 | Blumberg et al. .......... 436/161 |
| 6,257,047 B1 | * | 7/2001 | Grob et al. ................. 73/23.42 |
| 6,357,277 B1 | * | 3/2002 | Pigozzo et al. ............ 73/23.22 |
| 6,389,879 B1 | * | 5/2002 | Grob et al. ................. 73/23.42 |

\* cited by examiner

Primary Examiner—Hezron Williams
Assistant Examiner—David J. Wiggins

(57) ABSTRACT

A method applies retention-time locking to the retention times and/or the column(s) void times of a target analyte(s) being eluted thru a multidimensional gas chromatography system. Retention time locking is applied to both standard and comprehensive multidimensional gas chromatography via the steps of adjusting column(s) head pressure in a locking multidimensional gas chromatograph system such that the measured retention times and/or void times match the known accepted. Retention time locking may be applied to either or both of the columns in a multidimensional gas chromatography system. Additionally, if the multidimensional system contains more than two columns in series, retention time locking can be applied to any or all of the columns as required.

20 Claims, 4 Drawing Sheets

RETENTION-TIME LOCKED COMPREHENSIVE MULTIDIMENSIONAL GAS CHROMATOGRAPHY

TECHNICAL FIELD

The technical field is gas chromatography, and in particular, retention time locking and multidimensional gas chromatography.

BACKGROUND ART

Prior Art of Multidimensional Gas Chromatography

Multidimensional chromatography is technique that employs more than one separation stage (phase). Multidimensional gas chromatography is typically performed by coupling more than one gas chromatography column in series. The different columns usually have different stationary phases. The different stationary phases employ different separation mechanisms resulting in increased separation between the components of the sample. The columns are selected so that the components of interest in the sample will be separated in either one or the other or in combination of the two columns.

In standard multidimensional gas chromatography, the entire sample is introduced into the first column. The sample flows through the first column where the initial separation takes place. The sample is then transferred directly into the second column. The transferred sample then flows through the second column where the second separation takes place. Finally, the sample then flows from the second column directly into the detector.

There are several variations of the standard technique. Most commonly, only a portion of the sample is transferred from the first column into the second column. This technique, known as "heart cutting," is used to effect separations in especially complex mixtures. The portion transferred to the second column generally contains a much less complex subset mixture than the original sample. A less common variation of the standard method, known as splitting, directs a fraction of the sample exiting the first column into a detector and directs the remaining fraction into the second column. The main advantage of heart cutting is it allows the chromatographer to monitor the separation on the first column as well as the second column.

Comprehensive multidimensional gas chromatography (CMDGC) is another variation of the standard technique. CMDGC employs an additional step during the transfer of the sample between columns. The additional step periodically focuses and desorbs the sample at a transition stage between columns. The focusing-desorption of the sample is accomplished by thermal modulation of the sample at the transfer point between the columns. The sample is accumulated and "focused" at a point prior to the entrance of the second column. Focusing is usually accomplished by a cooling device that retains the sample. The focused sample is then heated in the desorption step, which accelerates a portion of the retained sample into the second column. The accelerated portion of the sample or "desorption" is performed at timed intervals. The focusing-desorption step has the effect of releasing concentrated pulses of sample into the carrier stream, thereby increasing separation and detectability in the second column.

The focusing-desorption step is computer controlled. The computer records the focus time and the desorption time. The focus time corresponds to the elution time for an analyte from the first column. The desorption time corresponds to the injection time of the analyte into the second column. Elution time and injection time allows the chromatographer to determine the elution time of the solutes from the first column as well as the elution time of the second column.

The typical output from a CMDGC is a three dimensional (3D) plot with axes corresponding to retention time on the first and second column (usually x and y-axes), and the detector response representing the z-axis. Alternately, the 3D plot may be collapsed into "iso" plots that represent a top-down (x and y-axes) view of the standard 3D plot.

With all types of multidimensional gas chromatography (GC), additional dimensions are possible with the addition of more columns or with detectors that provide multidimensional signals. Examples of multidimensional signal detectors include mass spectrometers, absorbance spectrometers, and emission spectrometers.

A disadvantage of standard and comprehensive multidimensional GC is that the retention times (the time it takes analytes to elute from a column) for single or multiple compounds can vary from instrument to instrument and even day to day on the same instrument. The variations, which can occur in each column of a multidimensional system, may be due to instrument drift, atmospheric changes, oven design, column dimension differences such as length or diameter, and stationary phase degradation.

The inconsistency of retention times increases the complexity of the resulting data. Inconsistency of retention times also disrupts the timing for heartcutting, thereby leading to inaccurate results. The data reduction and interpretation time resulting from these variations is increased significantly. The chromatographer must compensate for the variations or reanalyze the samples prior to interpreting the results each time a variation occurs. In effect, every data set containing a retention time variation must be evaluated as if it were a new method.

Prior Art of Retention-Time Locking

Retention-time locking is a technique that adjusts operational parameters of a gas chromatograph to avoid variations in retention time. Retention-time locking compensates for system, time-to-time, and location-to-location matching of retention times between known or reference systems and new or different systems.

Retention-time locking is accomplished through various methods. The only requirement of retention-time locking is that the columns used have the same stationary phase type (chemistry) and the same nominal phase ratio. Most commonly, the column head pressure on the new or different system is adjusted so that the column void time or the retention time of a known analyte equals a defined value (the defined value being ascertained on a reference system). Head pressure is most commonly regulated by a precise pressure controller. The adjusted head pressure compensates for differences in column and operational parameters producing retention times identical or nearly identical to those of the reference system.

Some varieties of pressure controllers can also react and adjust to changes in operating conditions including, for example, changes in ambient (atmospheric) pressure and temperature fluctuations. The added control can help to fine tune head pressure and provide even better retention time stability.

Retention time locking can be utilized in combination with other chromatographic techniques such as, for example, method translation and retention time factors. Method translation is a process that allows one to predictably scale a known set of chromatographic conditions in response to a desired change in one or more system parameters. Functions that relate gas flow rate in the column to column dimensions (length and diameter), temperature, carrier gas type, stationary phase film thickness, inlet pressure, and outlet pressure are used to calculate appropriate new sets of conditions. Using method translation, peak elution order and relative retention are maintained, and retention times of analytes are precisely predicted. Because there is usually some uncertainty in the exact column dimensions, oven temperature, and stationary film thickness, method translation can be followed by retention time locking to better match new retention times to a predicted retention time on a reference system.

Retention factors represent normalized retention times. Considering that GC methods can be scaled, reduced representations of retention time resulting from locked but scaled methods can be more easily compared or used. For example, results from a reference GC can be searched against the same library of retention factors for a scaled GC system that is running at fives times the speed of the reference system. If retention factors were not used, either the chromatographic data from the faster system would have to be multiplied by 5, or the data in the library would have to be divided by 5 prior to searching. The concept of using retention factors with retention time locked GC systems is highlighted in U.S. Pat. No. 6,153,438.

SUMMARY

A method applies retention-time locking to multidimensional gas chromatography. Retention time locking is applied to both standard and comprehensive multidimensional gas chromatography. The method simplifies data interpretation compared to conventional methods. The consistency of retention times generated by the method allows users to reduce time spent correlating data generated over time and between instruments. The consistency of retention times also allows the creation of a general compound library or map that can be used for compound identification, compound class identification and determining the chemical nature and properties of sample components on any similar multidimensional GC system operated under locked conditions.

In an embodiment, retention time locking may be applied to either or both of the columns in a multidimensional gas chromatography system. Additionally, if the multidimensional system contains more than two columns in series, retention time locking can be applied to any or all of the columns as required.

DETAILED DESCRIPTION

A method for retention time locking a multidimensional GC is described. The method applies to a multidimensional GC system containing more than one column as well as to comprehensive multidimensional GC systems with one or more focusing and desorption sites. A method for generating a general compound map that is consistent between multidimensional system is also disclosed.

Figure 1:
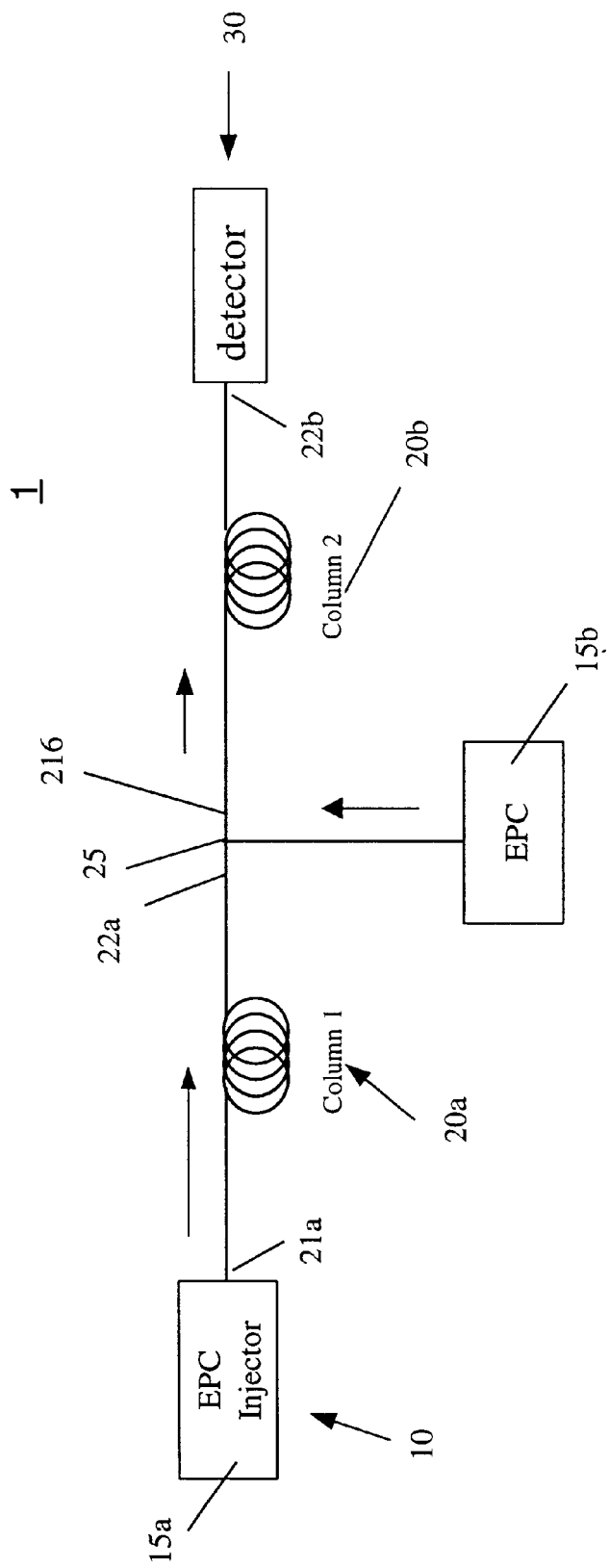
FIG. 1 diagrams a basic multidimensional GC configured for retention time locking.

FIG. 1 diagrams a basic multidimensional GC system 1 configured for retention time locking. The basic multidimensional GC system 1 includes two columns 20a and 20b connected in series. Columns 20a and 20b have inlets 21a and 21b and outlets 22a and 22b respectively, with corresponding outlet pressures and inlet pressures (also known as head pressure). A sample introduction source 10 is positioned at the inlet 21a of the first column 20a. The preferred sample introduction source 10 is a chromatographic inlet, however other sample introduction sources may be used including, for example, valves, thermal desorbers, pyrolyzers, headspace, and solid phase micro extraction. A precise pressure controller 15a is also positioned at the inlet 21 a of the first column 20a. A precise pressure controller controls the head pressure of the column it to which it is connected. In FIG. 1 the precise pressure controller 15a controls the head pressure of the first column 20a. The preferred precise pressure controller is an Electronic Pneumatic Control (EPC), however, others controllers may be used including, for example, traditional single or multiple stage pressure controllers. The outlet 22a of the first column 20a and the inlet 21b of the second column 20b are connected at a junction 25a. A second precise pressure controller 15b is positioned at the junction 25a between the first column 20a and the second column 20b. Again, the preferred precise pressure controller 15b is an EPC. The second precise pressure controller 15b controls the head pressure of the second column 20b. A detector 30 is positioned at the outlet 22b of the second column 20b. The detector 30 can be any detector used in the art. The choice of detector 30 will depend on the specific requirements of the chromatographic method employed. No single detector 30 is preferred because different detectors 30 are more suitable for different analyses. If desired, the detector 30 can be replaced by another useful device, such as a fraction collector for example, or removed altogether.

In operation, carrier gas flows, with or without solutes from the sample introduction source 10, from the inlet 21a of the first column 20a through the first column 20a, and is joined at the junction 25, with flow from the second precise pressure controller 15b. Thereafter, the combined flow continues through the second column 20b to the detector 30. Samples reach the detector 30 after traveling through both columns 20a and 20b The preferred method of retention time locking the multidimensional chromatography system 1 is to lock the overall retention time; the overall retention time is the sum of the individual retention times for the first column 20a and the second column 20b. Locking the overall retention time is accomplished by retention time locking both columns 20a and 20b. The preferred way to lock the overall retention time is to lock the second column 20b first and the first column 20a second. Locking the overall retention time in this order is most straightforward because the head pressure of the second column 20b is the outlet pressure of the first column 20a.

Locking the overall retention time on the two column multidimensional GC system 1 is accomplished by performing the following steps: (1) configuring operating parameters of a reference multidimensional GC system in accordance with a known chromatographic method, wherein the reference multidimensional GC system includes a first column and a second column connected in series, each of the columns having a known stationary phase, nominal diameter and length, and phase ratio; (2) injecting one or more known analytes into the reference multidimensional GC system yielding defined analyte retention times and/or defined void times for each column; (3) configuring operating parameters of a locking mulitidmensional GC system in accordance with the known chromatographic method, wherein the locking multidimensional GC includes a first column and a second column, each of the columns having a same known stationary phase, nominal diameter and length and phase ratio as the reference multidimensional GC system and wherein the first column and second column have a head pressure; (4) adjusting the head pressure of the second column such that the retention times of the known analytes and/or void time for the second column are matched to the corresponding defined analyte retention times and/or defined void time; and (5) adjusting the head pressure of the first column such that the retention times of the known analytes and/or void time for the second column are matched to the corresponding defined analyte retention times and/or defined void time.

Several methods for calculating and/or determining the appropriate adjustments to the head pressure are known in the art such as, for example, the empirical approach or standard mathematical relationships for void time calculations. Any known method can be used, however the preferred method is described in U.S. Pat. No. 5,987,959 and is incorporated herein by reference as if fully set forth. These methods require the retention times of analytes on individual columns be able to be determined.

The retention time of analytes or void time on the second column 20b may be determined directly by introducing one or more known analytes or a non-retained component at the junction 25 between the columns 20a and 20b. This can be accomplished by using a sample introduction source 10 as the source of the pressure 15b between the first column 20a and the second column 20b.

Once locked, the retention time of analytes or void time on the first column 20a may be determined indirectly by introducing one or more known analytes or a non-retained component into the sample introduction source 10 yielding a total retention time for both columns. The retention time for the analyte in the first column 20a is calculated by subtracting the retention time of the second column 20b (which is known because the second column 20b is locked) from the total retention time.

Although retention time locking the entire system is the preferred method, either the first column 20a or the second column 20b may be individually retention time locked without locking the remaining column. Retention time locking and individual column in a multidimensional GC system is accomplished by controlling the precise head pressure controller connected to the individual column to be locked.

Figure 2:
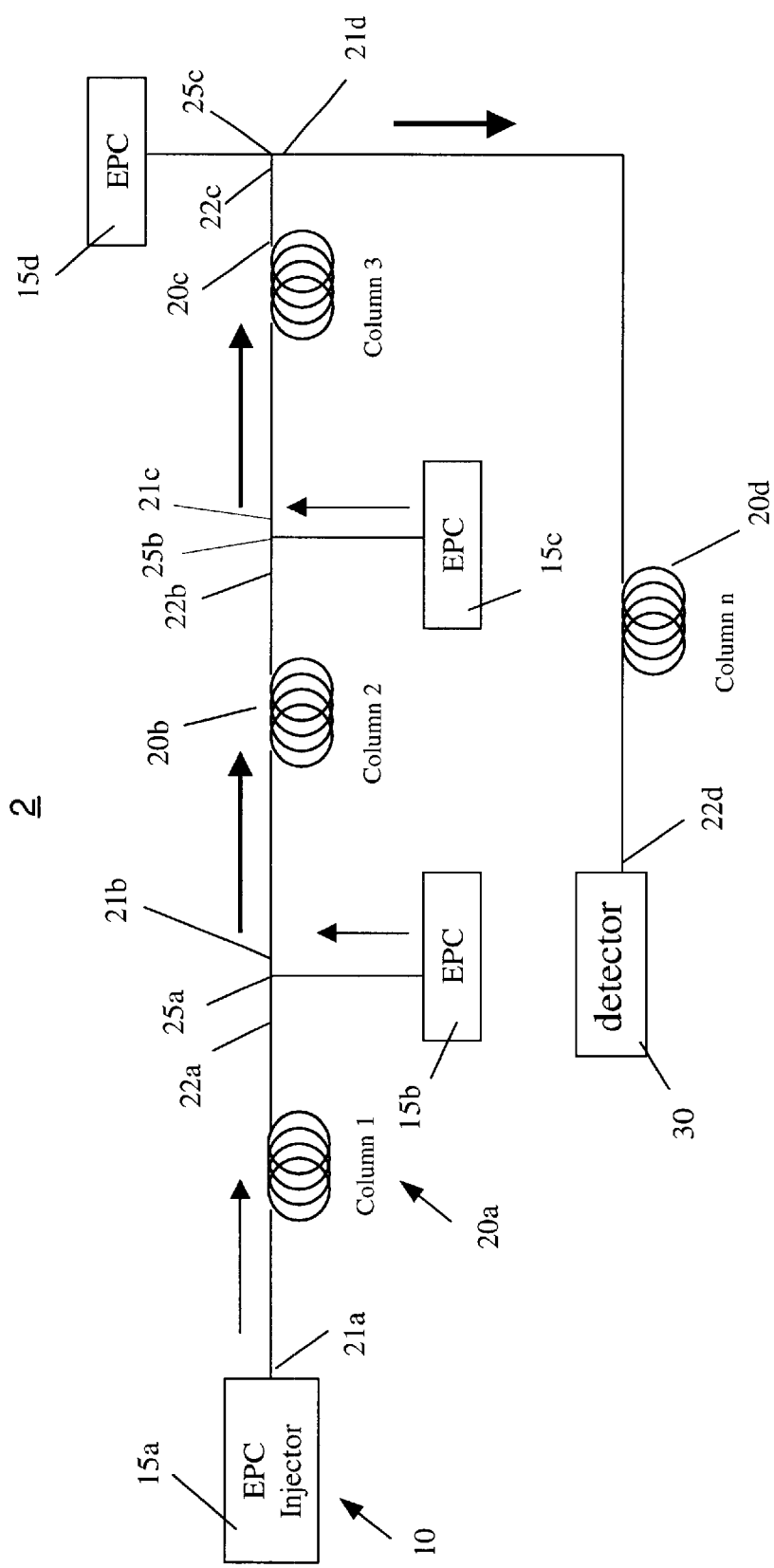
FIG. 2 diagrams a multidimensional GC with additional columns configured for retention time locking.
Figure 3:
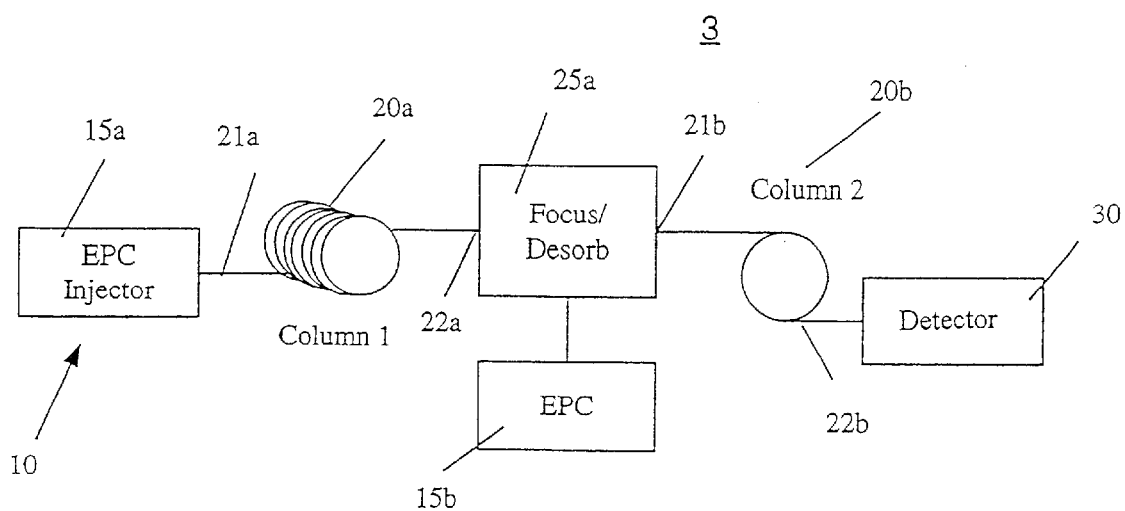
FIG. 3 diagrams a comprehensive multidimensional GC configured for retention time locking.

The method used to retention time lock the basic multidimensional GC system 1 described in FIG. 1 may be applied to any variation of the basic system 1. FIGS. 2 and 3, for example, show other embodiments of the basic system to which the method of this invention can be applied. In general, the discussion of the components in FIG. 1 applies to the components in FIGS. 2 and 3 unless otherwise noted. Columns 20a and 20b have inlets 21a and 21b and outlet 22a and 22b, respectively, with corresponding outlet pressures and inlet pressures. A sample introduction source 10 is positioned at the inlet 21a of the first column 20a. A precise pressure controller 15a is also positioned at the inlet 21a of the first column 20a and a second precise pressure controller 15b is positioned at the junction 25a between the first column 20a and the second column 20b.

The system 2 of FIG. 2 deviates from the basic system at the outlet 22b of the second column 20b. The outlet 22b of the second column 20b is connected to an inlet 21c of a third column 20c at a second junction 25b. A third precise pressure controller 15c is positioned at the second junction 25b. The third precise pressure controller 15c controls the head pressure of the third column 20c. The outlet 22c of the third column 20c is connected to an inlet 21d of a fourth column 20d at a third juncture 25c. A fourth precise pressure controller 15d is positioned at the third juncture 25c. The fourth precise pressure controller 15d controls the head pressure of the fourth column 20d. An outlet 22d of the fourth column 20d is connected to a detector 30.

The use of four columns connected in series in FIG. 2 is illustrative. Retention time locking can be applied to any multidimensional GC systems with more than one column. Each column to be retention time locked in a multidimensional GC system may use a precise pressure controller to control the head pressure of that column. As with the basic multidimensional GC system 1, the preferred method of retention time locking a multidimensional GC system with 3 or more columns is to lock the overall retention time for the entire system. Locking the overall retention time requires that each column of a system be retention time locked. The preferred method for locking a multidimensional GC system with 3 or more columns is to lock the columns sequentially, starting with the last column and proceeding to the first column. Using FIG. 2 as an example, in order to lock the overall retention time, the fourth column 20d is locked first, the third column 20c is locked with 3 or more columns is to lock the columns sequentially, starting with the last column and proceeding to the first column. Using FIG. 2 as an example, in order to lock the overall retention time, the fourth column 20d is locked first, the third column 20c is locked second, the second column 20b is locked third, and the first column 20a is locked last. Once all the columns are locked, the overall retention time is locked.

As with the basic multidimensional GC system 1, any individual column or combination of columns can be retention time locked in a multidimensional GC system with 3 or more columns. This is accomplished by controlling the precise pressure controller connected to the column or combination of columns to be locked.

Locking the retention time of one or more columns on a multidimensional GC system is accomplished by performing the following steps: (1) configuring operating parameters of a reference multidimensional GC system in accordance with a known chromatographic method, wherein the reference multidimensional GC includes more than one column connected in series, each of the columns having a known stationary phase, nominal diameter and length, and phase ratio; (2) introducing one or more target analytes into the reference multidimensional GC system yielding defined analyte retention times and/or defined void times for one or more columns of the reference multidimensional GC; (3) configuring operating parameters of a locking multidimensional GC system in accordance with the known chromatographic method, wherein the locking multidimensional GC system includes a same number of columns connected in series as the reference multidimensional GC system, each of the same number of columns having a same known stationary phase, nominal diameter and length and phase ratio as the reference multidimensional GC system and wherein each column of the locking multidimensional GC system has a head pressure; (4) locking the retention times of the target analytes or void times on one or more columns of the locking multidimensional GC system, beginning with a last column in series to be locked and proceeding sequentially to a first column to be locked, by adjusting the head pressure of the column to be locked such that the retention times of the target analytes or column void times on the locking multidimensional GC system are matched to the corresponding defined analyte retention times and/or defined column void times.

FIG. 3 depicts a comprehensive multidimensional GC system 3 configured for retention time locking. The comprehesnsive multidimensional GC system 3 is set up similar to the basic multidimensional GC system 1 except a focus-desorption device is positioned at the junction 25a between the first column 20a and the second column 20b. The focus-desorption device does not replace the precise pressure controller 15b, but is connected at the junction 25a in addition to the precise pressure controller 15b. Traditional (non-retention time locked) comprehensive multidimensional gas chromatography does not use a pressure controller between the first and second columns; however the second precise pressure controller is necessary in the system 3 of FIG. 3 to retention time lock the second column.

As with other multidimensional GC systems, the preferred method for retention time locking the comprehensive multidimensional GC system 3 is to lock the overall retention time. This is accomplished by locking both columns 20a and 20b in the system 3. The preferred method of locking the overall retention time of the system 3 is to lock the second column 20b first and lock the first column 20a second.

The retention time of analytes or void time on the second column on a comprehensive multidimensional GC can be computed directly. The focusing-desorption device is computer controlled. The time of desorption of an analyte at the junction between columns is the injection time for that analyte into the second column 20b, so the retention time of that analyte for the second column 20b can be computed directly. Similarly, the retention time or void time on the first column 20a may also be computed directly because the time of focusing for an analyte represents the retention time of that analyte for the first column 20a.

Although retention time locking the entire multidimensional GC system 3 is the preferred method, either the first column 20a or the second column 20b may be individually retention time locked without locking the remaining column. This is accomplished by controlling the precise pressure controller connected to the individual column to be locked.

The system 3 of FIG. 3 illustrates how retention time locking can be used on a comprehensive multidimensional GC system. Other comprehensive multidimensional GC systems can be configured for retention time locking. For example, additional columns, such as in FIG. 2 can be included in a comprehensive multidimensional GC system. Alternatively, a focus-desorption device can be placed at any junction between columns or at the inlet 21a at the first column or at the outlet of the last column in series before the detector 30.

Retention time locking of any of the abovementioned multidimensional GC systems can be implemented in combination with other known chromatography techniques such as scaling of conditions or a retention factor approach. Throughout this application, any reference to multidimensional GC includes comprehensive multidimensional GC unless otherwise noted.

Retention time locked multidimensional GC conditions can be scaled exactly. When scaling the conditions of a locked multidimensional GC method, the method is first translated using the technique of "method translation," followed by retention time locking the scaled method. The technique of method translation is described in "PreciseTime-Scaling of Gas Chromatographic Methods Using Method Translation and Retention Time Locking Application", B. D. Quimby, L. M. Blumberg, M. S. Klee, and P. L. Wylie, Agilent Technologies Application Note 5967-5820E, 3/2000 and U.S. Pat. No. 5,405,432, both of which are incorporated herein by reference as if fully set forth. The scaling of conditions of a retention time locked multidimensional GC enables the user to respond to changing requirements of an analysis.

For example, if the user requires a decreased analysis time, a shorter column or a column with a smaller internal diameter can replace the column called for by the method. The replacement column may produce a shorter analysis time with known speed gain for all analytes. The resulting scaled method can then be retention time locked producing an exactly scaled method. Any or all of the individual columns of a locked multidimensional GC system can be scaled depending on the user's requirements. For example, the analysis time of the initial separation in the first column can be changed while maintaining the separation speed of the second column, or alternatively, the separation speed of the second column can be changed while maintaining the separation speed of the first.

The results or data produced by various scaled conditions of a common retention time locked multidimensional GC system can easily be compared against the original conditions or against differently scaled conditions by implementing a retention time factor approach. The retention time factor approach converts retention times of an analysis to retention factors. Retention factors are retention times normalized to void time or locked reference time. The method for converting retention times into retention factors is described in U.S. Pat. No. 6,153,438 and is incorporated herein by reference as if fully set forth. The time normalization that results from the conversion of retention times reduces retention times to a common scale.

A retention time or retention factor locked multidimensional GC system may be used for creating a general compound map that is consistent between locked multidimensional GC systems.

Figure 4:
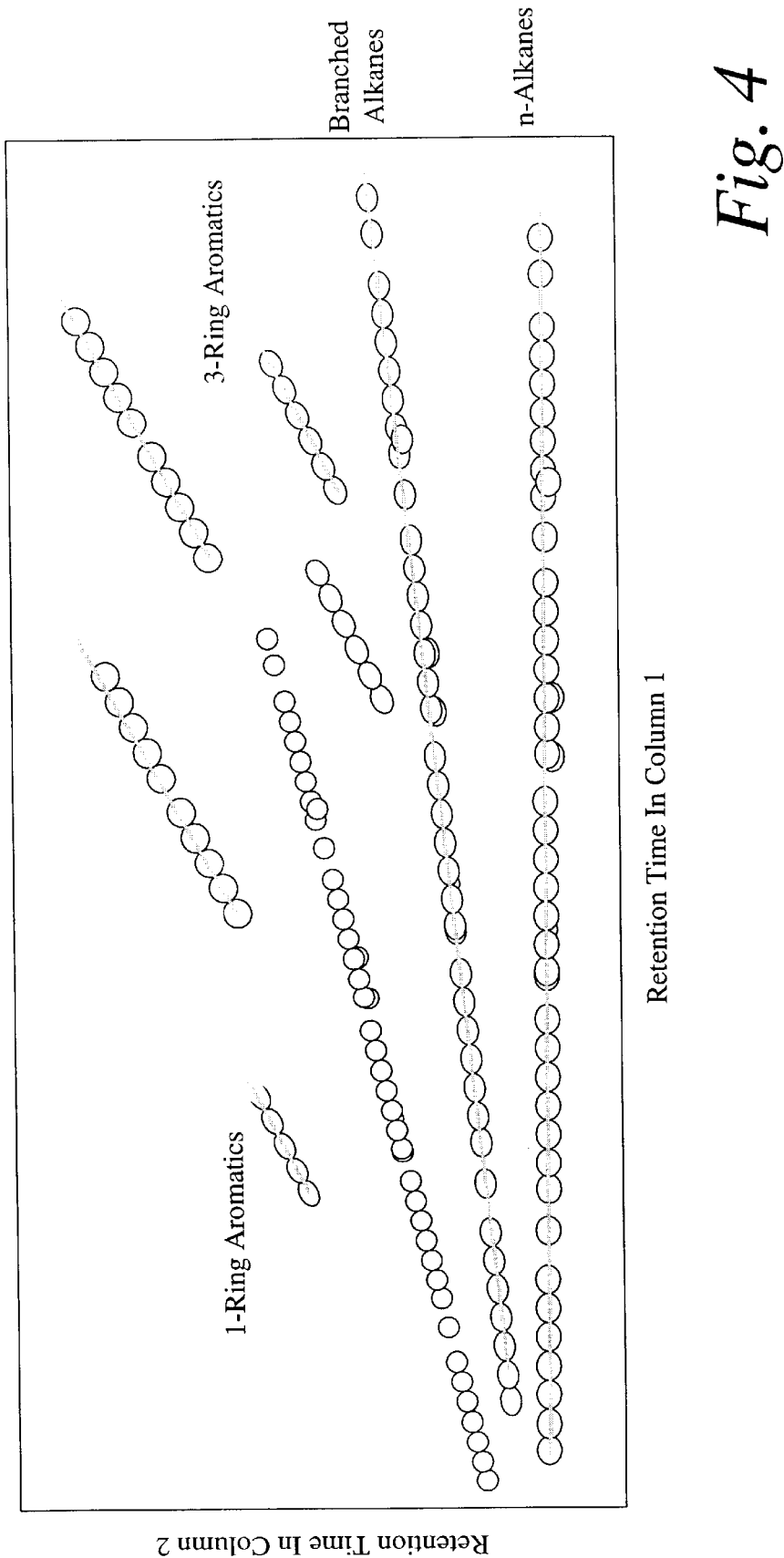
FIG. 4 depicts an iso plot for multidimensional GC.

FIG. 4 depicts an iso plot for multidimensional GC configured with two columns. In FIG. 4 multidimensional chromatographic space is represented by axes. The x-axis represents the retention time for analytes eluting from the first column. The y-axis represents the retention time for analytes eluting from the second column. The circles within the chart represent specific compounds that have been separated through the combined set of both the first and second column. Typically, concentric circles are used to indicate signal intensity, however other methods are used such as color, for example. The lines illustrate typical patterns that result for the elution of homologs.

General compound maps can be created for multidimensional GC systems operated under locked conditions. The general compound map may be used to identify compounds on any multidimensional GC system operated under the same locked conditions as the reference multidimensional GC system used to create the general compound map. Additionally, general compound maps may be used with scaled and locked systems and with corresponding retention factor normalization. Alternatively, a retention time database of the defined analytes retention times may be created. The data points in multidimensional chromatographic space may be stored in a database.

The method for creating a compound map comprises injecting a series of known analytes into a reference system under locked conditions and generating a retention time database. The reference system must have the overall retention time locked. Each analyte injected will produce corresponding retention time data for each column in the reference system. For example, if the reference system has two columns (a and b) connected in series, each known analyte injected will have a corresponding retention time for column a and a corresponding retention time for column b. The values obtained are placed in a database and form the basis for identification of unknowns eluting at specific times from columns a and FIG. 4 depicts an iso plot for multidimensional GC configured with two columns. In FIG. 4 multidimensional chromatographic space is represented by axes. The x-axis represents the retention time for analytes eluting from the first column. The y-axis represents the retention time for analytes eluting from the second column. The circles within the chart represent specific compounds that have been separated through the combined set of both the first and second column. Typically, concentric circles are used to indicate signal intensity, however other methods are used such as color, for example. The lines illustrate typical patterns that result for the elution of homologs.

General compound maps can be created for multidimensional GC systems operated under locked conditions. The general compound map may be used to identify compounds on any multidimensional GC system operated under the same locked conditions as the reference multidimensional GC system used to create the general compound map. Additionally, general compound maps may be used with scaled and locked systems and with corresponding retention factor normalization. Alternatively, a retention time database of the defined analytes retention times may be created. The data points in multidimensional chromatographic space may be stored in a database.

The method for creating a compound map comprises injecting a series of known analytes into a reference system under locked conditions and generating a retention time database. The reference system must have the overall retention time locked. Each analyte injected will produce corresponding retention time data for each column in the reference system. For example, if the reference system has two columns (a and b) connected in series, each known analyte injected will have a corresponding retention time for column a and a corresponding retention time for column b. The values obtained are placed in a database and form the basis for identification of unknowns eluting at specific times from columns a and b.

The reference system must also be configured so that the retention times of the analytes can be monitored after they elute from each individual column in the system. Techniques for accomplishing this are known in the art and any appropriate technique may be used. If the reference system is a comprehensive multidimensional GC, the focus-desorption step performs the function of indicating elution time from a column.

The two (or more if the reference system has more than two columns) retention times associated with each analyte can be plotted, such as on an iso-plot as shown in FIG. 4. Each analyte has a "position" on the iso-plot. Unless two different analytes have identical retention times for both columns, then each analyte has a unique position on the iso-plot. The retention time database and/or the iso-plot for a given reference column is a compound map that is consistent over time and between instruments and practitioners.

Any of the above described multidimensional GC systems can be equipped with a selective detector. Most selective detectors can be "tuned" to respond to specific attributes of eluting compounds. For example, a mass spectrometer detector can be tuned to detect ions with a specific mass/charge ratio or a photo diode array detector can be tuned detect compounds that emit a specific wavelength. By locking the multidimensional GC system, the user can more accurately program the selective detector to detect certain attribute at the precise time the target analyte is eluting.

I claim:

1. A method of retention time locking a multidimensional GC system, comprising:
    (i) configuring operating parameters of a reference multidimensional GC system in accordance with a known chromatographic method, wherein the reference multidimensional GC system includes more than one column connected in series, each of the columns having a known stationary phase, nominal diameter and length, and phase ratio;
    (ii) introducing one or more target analytes into the reference multidimensional GC system yielding defined analyte retention times and/or defined void times for one or more columns of the reference multidimensional GC system;
    (iii) configuring operating parameters of a locking multidimensional GC system in accordance with the known chromatographic method, wherein the locking multidimensional GC system includes a same number of columns connected in series as the reference multidimensional GC system, each of the same number of columns having a same known stationary phase, nominal diameter and length and phase ratio as the reference multidimensional GC system and wherein each column of the locking multidimensional GC system has a head pressure;
    (iv) locking the retention times of the target analytes or void times on one or more columns of the locking multidimensional GC system, beginning with a last column in series to be locked and proceeding sequentially to a first column to be locked, by adjusting the head pressure of the column to be locked such that the retention times of the target analytes or column void times measured on the locking multidimensional GC system are matched to the corresponding defined analyte retention times and/or defined column void times.

2. The method of claim 1, further comprising locking all of the columns of the locking multidimensional GC system.

3. The method of claim 1, further comprising converting the retention times of the analytes to retention factors and locking the columns on the locking multidimensional GC system based on retention factors.

4. The method of claim 1, wherein the reference multidimensional GC system and the locking multidimensional GC system are comprehensive multidimensional GC systems.

5. The method of claim 1, further comprising scaling the conditions of one or more of the columns of the locking multidimensional GC system.

6. The method of claim 5, wherein the scaling is accomplished by method translation.

7. The method of claim 1 wherein the reference multidimensional GC system includes a multidimensional detector.

8. The method of claim 7, further comprising tuning the multidimensional detector to respond to specific attributes of the analytes.

9. The method of claim 1 further comprising generating a retention time database of the defined analyte retention times in multidimensional chromatographic space.

10. The method of claim 9 further comprising plotting the defined analyte retention time to create an isoplot.

11. The method of claim 10 further comprising generating a set of homolog vectors in the multidimensional chromatographic space.

12. A method of locking the overall retention time of a multidimensional GC system comprising:
(i) configuring operating parameters of a reference multidimensional GC system in accordance with a known chromatographic method, wherein the reference multidimensional GC system includes two or more columns connected in series, each of the columns having known stationary phase, nominal diameter and length, and phase ratio;
(ii) introducing one or more known analytes into the reference multidimensional GC system yielding defined analyte retention times and/or defined void time for each column;
(iii) configuring operating parameters of a locking multidimensional GC system in accordance with the known chromatographic method wherein the locking multidimensional GC system includes a same number of columns connected in series, each of the same number of columns having a same known stationary phase, nominal diameter and length, and phase ratio as the reference multidimensional GC system and wherein each column of the locking multidimensional GC system has a head pressure;
(iv) locking the retention times of the known analytes or void times on the locking multidimensional GC system by adjusting the head pressures of each column on the locking multidimensional GC system, beginning with a last column in series and proceeding sequentially to a first column in series, such that the retention times of the known analytes or column void times measured on the locking multidimensional GC system are matched to the corresponding defined analyte retention times and/or defined column void time.

13. The method of claim 12, wherein the reference multidimensional GC systems and the locking multidimensional GC systems are comprehensive multidimensional GC systems.

14. The method of claim 12, further comprising converting the retention times of the analytes to retention factors and locking the columns on the locking multidimensional GC system based on retention factors.

15. The method of claim 12, further comprising scaling the conditions of one or more of the columns of the locking multidimensional GC system.

16. The method of claim 15, wherein the scaling is accomplished by method translation.

17. A method of retention time locking a multidimensional GC system comprising:
(i) configuring operating parameters of a reference multidimensional GC system in accordance with a known chromatographic method, wherein the reference multidimensional GC system includes a first column and a second column connected in series, each of the columns having a known stationary phase, nominal diameter and length, and phase ratio;
(ii) injecting one or more known analytes into the reference multidimensional GC system yielding defined analyte retention times and/or defined void times for each column;
(iii) configuring operating parameters of a locking mulitidmensional GC system in accordance with the known chromatographic method, wherein the locking multidimensional GC includes a first column and a second column, each of the columns having a same known stationary phase, nominal diameter and length and phase ratio as the reference multidimensional GC system and wherein the first column and second column have a head pressure;
(iv) adjusting the head pressure of the second column such that the retention times of the known analytes and/or void time measured for the second column are matched to the corresponding defined analyte retention times and/or defined void time;
(v) adjusting the head pressure of the first column such that the retention times of the known analytes and/or void time for the second column are matched to the corresponding defined analyte retention times and/or defined void time.

18. The method of claim 17, wherein the reference multidimensional GC system and the locking multidimensional GC system are comprehensive multidimensional GC systems.

19. The method of claim 17 further comprising converting the retention times of the analytes to retention factors and locking the columns on the locking multidimensional GC system based on retention factors.

20. The method of claim 10 further comprising using the retention time database, isoplot and/or homolog vectors to identify unknown analytes on the locking multidimensional GC system.

* * * * *